June 13, 1950 W. B. CLARKE Plant Pat. 946
LILAC PLANT
Filed June 13, 1949
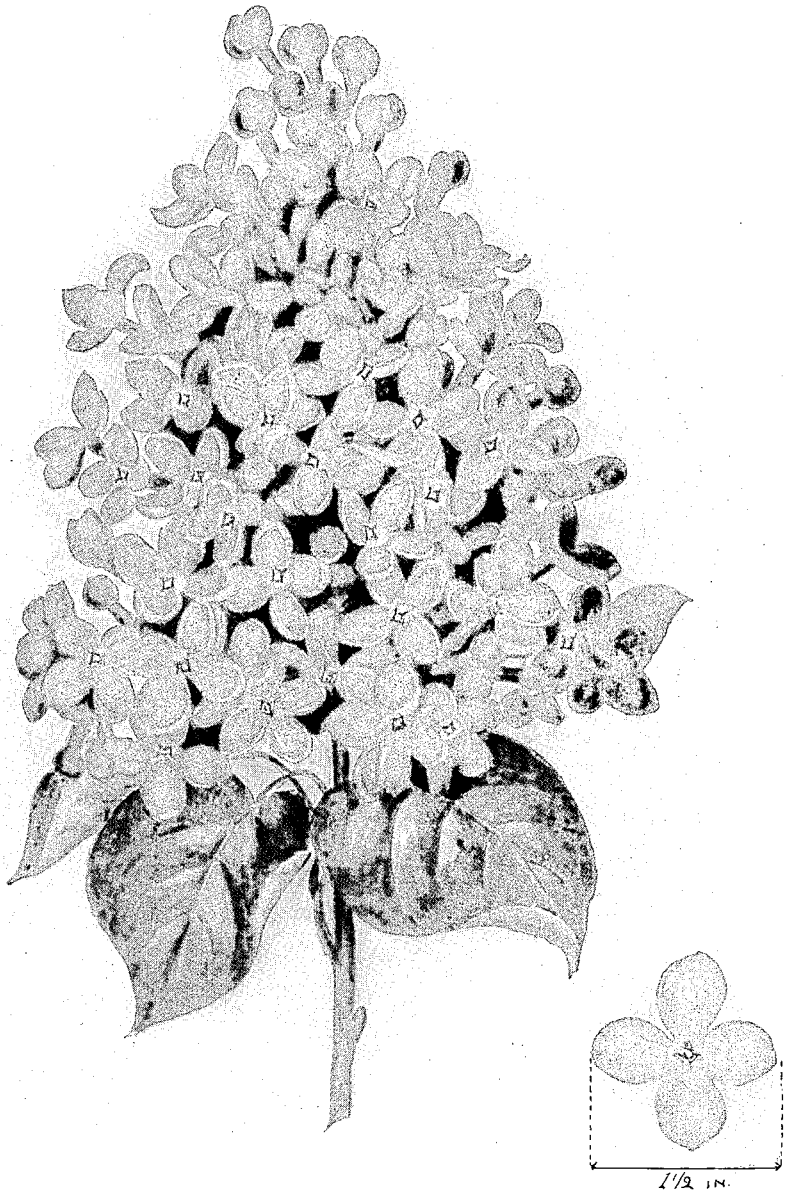
WITNESS
Addison J. Avery
INVENTOR
WALTER BOSWORTH CLARKE,
by Rummler, Rummler & Snow,
ATTYS.

Patented June 13, 1950

Plant Pat. 946

UNITED STATES PATENT OFFICE

946

LILAC PLANT

Walter Bosworth Clarke, San Jose, Calif., assignor to W. B. Clarke & Co., San Jose, Calif., a partnership Application June 13, 1949, Serial No. 98,765

1 Claim. (Cl. 47—60)

The present discovery relates to a new and distinct variety of lilac plant or *Syringa vulgaris*, resulting from a cross made by me between a seedling of an unnamed double variety as the seed parent and another unnamed seedling as the pollen parent.

Its novelty resides primarily in the dark purple coloring of the flowers which is retained from the bud stage to the fully opened flower, and the great size of the individual florets. The flowers open perfectly flat but later the petals (corolla lobes) may become slightly concave on the upper surface. The clusters of florets are of pyramidal or conical shape and usually are neither paired nor compound. The blooming season is medium late and of long duration so that the plant stays in flower until very late. This new lilac plant is the result of definite breeding efforts carried on by me and my associates since 1931. Asexual reproduction by budding and grafting has been carried on at Santa Clara County, California, and has proved these features to be firmly fixed.

The accompanying illustration shows a typical flower cluster in the main view and a face view of a single floret indicating its flat opening form and size.

The following is a detailed description of the distinguishing features of this new variety, the identification of flower colors being according to Horticultural Colour Chart, published in 1938 by The British Colour Council in collaboration with The Royal Horticultural Society:

Parentage: Seedling.
- *Seed parent.*—Unidentified double.
- *Pollen parent.*—Unknown.

Classification: *Syringa vulgaris* var.

Blooming habit: Usual. Time of blooming is medium late but it has a long season so stays in flower until very late.

Bud:
- *Size.*—Usual.
- *Form.*—Globular.
- *Color.*—Dark purple, according to British Horticultural Colour Chart, 733/3.

Flower:
- *Size of floret.*—Maximum 1½ inches in span.
- *Borne.*—In conical clusters, usually neither paired nor compound.
- *Petalage.*—Single. Petals open flat but finally become concave on upper surface.
- *Color.*—Doge Purple, identified in British Horticultural Colour Chart, 732/2.
- *Fragrance.*—Normal and good.
- *Disease resistance.*—Normal.

Plant:
- *Form.*—Bush.
- *Height.*—The plant is of moderate vigor and will probably become medium in size. No old ones in existence.

One of the outstanding qualities of this new variety is the large size and flat opening of its flower petals. The petals (corolla lobes) of most other large-flowered, deep purple lilacs are very strongly concave above. The buds open a Doge Purple and with age gradually become violet purple, the general tonal effect of the fully opened clusters being Doge Purple.

Another distinguishing feature of this new variety is the near uniformity of its purple coloring from the bud stage to the fully open flower, which in combination with its long blooming season and large size of its blooms and florets is a valuable asset for it as a commercial product.

Having thus disclosed my invention, I claim:

A new and distinct variety of *Syringa vulgaris* plant, substantially as illustrated and described, characterized as to novelty by the large size of its florets, their tendency to open in flat form, the uniformity of its distinctive purple coloring from bud stage to the fully open flowers, and its long-blooming season.

WALTER BOSWORTH CLARKE.

REFERENCES CITED

The following references are of record in the file of this patent:

UNITED STATES PATENTS

| Number | Name | Date |
|---|---|---|
| Pl. Pt. 832 | Clarke | Apr. 12, 1949 |